US010695509B2

(12) United States Patent
Kavokin et al.

(10) Patent No.: US 10,695,509 B2
(45) Date of Patent: Jun. 30, 2020

(54) NEGATIVE PRESSURE INJECTION DEVICE

(71) Applicant: BIOPREME MEDICAL TECHNOLOGIES INC., Chemainus (CA)

(72) Inventors: Alexsandr Kavokin, Moscow (RU); Nigel Anthony Syrotuck, Victoria (CA); Mark Sasha Drlik, Victoria (CA)

(73) Assignee: BIOPREME MEDICAL TECHNOLOGIES INC., Chemainus, British (CA)

( * ) Notice: Subject to any disclaimer, the term of this patent is extended or adjusted under 35 U.S.C. 154(b) by 136 days.

(21) Appl. No.: 15/768,657

(22) PCT Filed: Nov. 25, 2016

(86) PCT No.: PCT/CA2016/051396
§ 371 (c)(1),
(2) Date: Apr. 16, 2018

(87) PCT Pub. No.: WO2017/088066
PCT Pub. Date: Jun. 1, 2017

(65) Prior Publication Data
US 2018/0311444 A1 Nov. 1, 2018

Related U.S. Application Data

(60) Provisional application No. 62/260,504, filed on Nov. 28, 2015.

(51) Int. Cl.
*A61M 5/42* (2006.01)
*A61M 5/32* (2006.01)
(Continued)

(52) U.S. Cl.
CPC .............. *A61M 5/425* (2013.01); *A61M 5/30* (2013.01); *A61M 5/32* (2013.01); *A61M 5/42* (2013.01);
(Continued)

(58) Field of Classification Search
CPC ...... A61M 2205/3569; A61M 2205/52; A61M 2205/59; A61M 2205/6072; A61M 5/30;
(Continued)

(56) References Cited

U.S. PATENT DOCUMENTS 1,934,046 A 11/1933 Demarchi
2,743,723 A 5/1956 Hein
(Continued)

FOREIGN PATENT DOCUMENTS

CA 1189412 6/1985
CA 2 888 885 A1 4/2014
(Continued)

OTHER PUBLICATIONS www.biopreme.com, Biopreme Medical Technologies, Inc., JECT™ Soft-Assist Syringe Adaptor, Brochure, 2015, 2 Pages.
(Continued)

*Primary Examiner* — Brandy S Lee
(74) *Attorney, Agent, or Firm* — Davis & Bujold PLLC; Michael J. Bujold

(57) ABSTRACT

A negative pressure injection device which includes a suction cup and an inner skirt that encircles an injection port and depends into the interior of the suction cup. An injection member is surrounded by and protrudes below the inner skirt. When air is drawn from the suction cup an epidermis of a patient is drawn into the suction cup until the epidermis comes into contact with the inner skirt and that portion of the injection member protruding below the inner skirt. The inner skirt provides consistent epidermis positioning. The depth of (Continued)

injection is consistently defined by the extent to which the injection member protrudes below the inner skirt.

6 Claims, 5 Drawing Sheets

(51) Int. Cl.
*A61M 5/30* (2006.01)
*A61M 5/46* (2006.01)

(52) U.S. Cl.
CPC ............. *A61M 5/46* (2013.01); *A61M 5/3293* (2013.01); *A61M 2205/3569* (2013.01); *A61M 2205/52* (2013.01); *A61M 2205/59* (2013.01); *A61M 2205/6072* (2013.01)

(58) Field of Classification Search
CPC ........ A61M 5/32; A61M 5/3293; A61M 5/42; A61M 5/425; A61M 5/46
See application file for complete search history.

(56) References Cited

U.S. PATENT DOCUMENTS

| | | | |
|---|---|---|---|
| 4,284,077 A | 8/1981 | Wagner | |
| 4,299,219 A | 11/1981 | Norris, Jr. | |
| 4,723,940 A | 2/1988 | Wiegerinck | |
| 5,891,053 A | 4/1999 | Sesekura | |
| 5,911,703 A | 6/1999 | Slate et al. | |
| 6,200,291 B1 | 3/2001 | Di Pietro | |
| 7,833,170 B2 | 11/2010 | Matsumoto et al. | |
| 2003/0093032 A1 | 5/2003 | Py et al. | |
| 2004/0147901 A1* | 7/2004 | Py | A61M 5/2033 604/506 |
| 2005/0033234 A1 | 2/2005 | Sadowski et al. | |
| 2006/0293722 A1 | 12/2006 | Slatkine et al. | |
| 2007/0270745 A1 | 11/2007 | Nezhat et al. | |
| 2009/0054842 A1 | 2/2009 | Yeshurun et al. | |
| 2010/0249748 A1 | 9/2010 | Szucs | |
| 2015/0126963 A1* | 5/2015 | Despa | G06F 19/3456 604/506 |
| 2015/0246183 A1* | 9/2015 | Kavokin | A61M 5/30 604/506 |

FOREIGN PATENT DOCUMENTS

| | | |
|---|---|---|
| EP | 0 103 664 A1 | 3/1984 |
| EP | 0797951 A1 | 10/1997 |
| EP | 1 161 961 A1 | 12/2001 |
| EP | 1570783 A1 | 9/2005 |
| GB | 371 305 | 4/1932 |
| GB | 969781 A | 9/1964 |
| JP | 2001212231 A | 8/2001 |
| WO | 96/37148 A1 | 11/1996 |
| WO | 00/23132 A1 | 4/2000 |
| WO | 01/87389 A1 | 11/2001 |
| WO | 03/039369 A1 | 5/2003 |
| WO | 2004/004803 A2 | 1/2004 |
| WO | 2004/054445 A1 | 7/2004 |
| WO | 2005000382 A2 | 1/2005 |
| WO | 2007143377 A2 | 12/2007 |
| WO | 2010016635 A1 | 2/2010 |
| WO | 2015/062655 A1 | 5/2015 |

OTHER PUBLICATIONS www.biopreme.com, Biopreme Medical Technologies, Inc., JECT™ Needle-Free Syringe Adaptor, Brochure, 2014, 2 Pages.
www.biopreme.com, Biopreme Medical Technologies (Subsidiary of: Sonora Technologies, Inc.), JECT © Needle-Free Injection Device, Brochure, 2013, 2 Pages.
www.biopreme.com, Biopreme Medical Technologies, Inc., DermaQ™ Pediatric Needle-Phobia Solution, Brochure, 2017, 2 Pages.
European Search Report issued in corresponding European Patent Application No. 13846618.0 dated Jul. 1, 2016.
International Search Report Corresponding to PCT/CA2016/051396 dated Dec. 30, 2016.
Written Opinion Corresponding to PCT/CA2016/051396 dated Dec. 30, 2016.
International Preliminary Report on Patentability Corresponding to PCT/CA2016/051396 dated Feb. 26, 2018.
Supplementary European Search Report issued in corresponding European Patent Application No. 16 86 7496 dated Mar. 25, 2019.

* cited by examiner

300

Process Flow

1. Download/install QR Code app on mobile device

Start

Locate QR Code sticker on Biopreme™ Adaptor Device

Scan QR Code sticker using bar code app/reader on mobile device

Patients' self-administered injection regimen is tracked

End of Session

NEGATIVE PRESSURE INJECTION DEVICE

FIELD

There is described an injection device for medical and veterinary use that uses negative pressure to draw the epidermis upward to facilitate injection.

BACKGROUND

US Patent Publication 20150246183 (Kavokin) titled "Needle-free Injection Devices, Systems and Methods" discloses the theory of using negative pressure to draw the epidermis upward to facilitate injection.

During proto-type development and testing, problems of repeatability were encountered, which are hereinafter addressed. The problems of repeatability arose due to the differences between people. Some persons have a tight epidermis and some persons have a relatively loose epidermis. Some persons are small or underweight, and some persons are large or overweight. Even on the same person the properties of the epidermis may differ on different parts of their body.

SUMMARY

There is provided a negative pressure injection device which includes a suction cup having a top and a peripheral sidewall that define an interior and an exterior. An injection port through which liquid is injected extends from the exterior to the interior of the suction cup. An inner skirt encircles the injection port and depends into the interior of the suction cup. An injection member in fluid communication with the injection port. Injection member is surrounded by and protrudes below the inner skirt. A pressurization port extends from the interior to the exterior of the suction cup. When air is drawn from the suction cup through the pressurization port, the interior of the suction cup is pressurized to draw an epidermis of a patient into the suction cup until the epidermis comes into contact with the inner skirt and that portion of the injection member protruding below the inner skirt.

The negative pressure injection device, as described above, provides a repeatable injection. Regardless of skin type, the inner skirt always limits incursion of the epidermis into the interior of the suction cup and provides consistent epidermis positioning. The depth of injection is always defined by the extent to which the injection member protrudes below the inner skirt.

There were other changes made to make the negative pressure injection device more user friendly, which will hereinafter be described in more detail. One change involves the use of an injection member that is not part of a syringe. Another change involves providing a syringe coupling for coupling with a needle-free syringe on top of the suction cup. Yet another change involves positioning of a pressurization bulb along the peripheral sidewall.

BRIEF DESCRIPTION OF THE DRAWINGS

These and other features will become more apparent from the following description in which reference is made to the appended drawings, the drawings are for the purpose of illustration only and are not intended to be in any way limiting, wherein.

DETAILED DESCRIPTION

Figure 1:
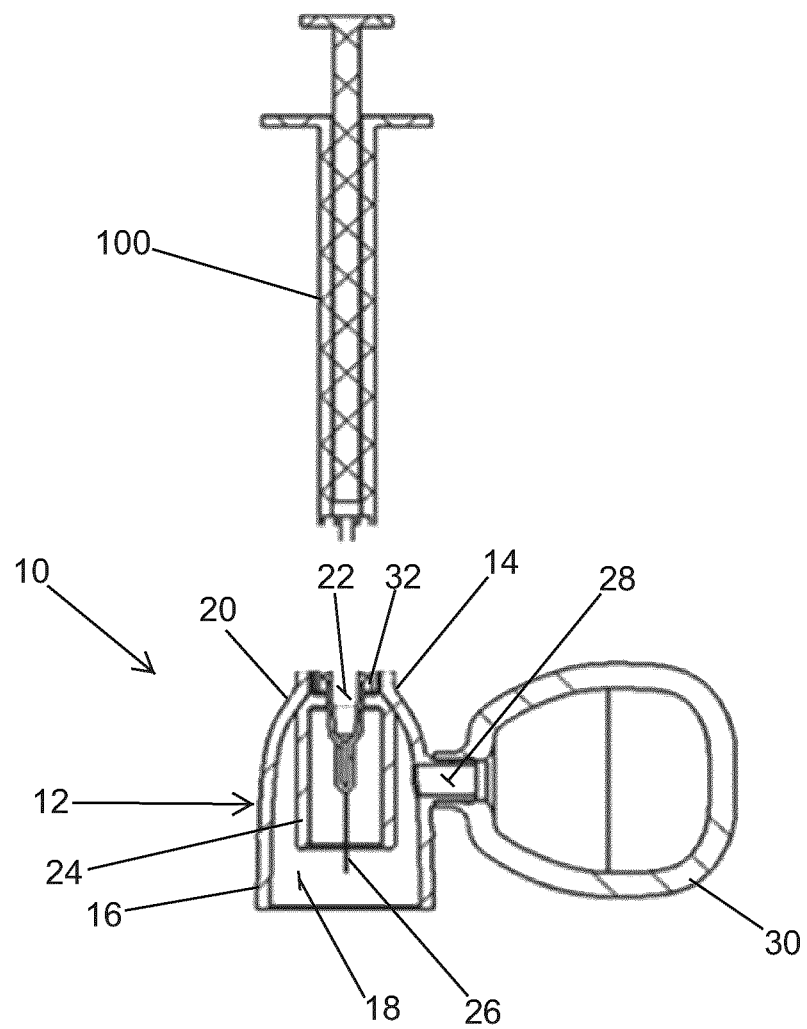
FIG. 1 is a side elevation view, in section, of the negative pressure injection device prior to coupling with a standard needle-free syringe.

A negative pressure injection device, generally identified by reference numeral 10, will now be described with reference to FIG. 1 through FIG. 7.

Figure 3:
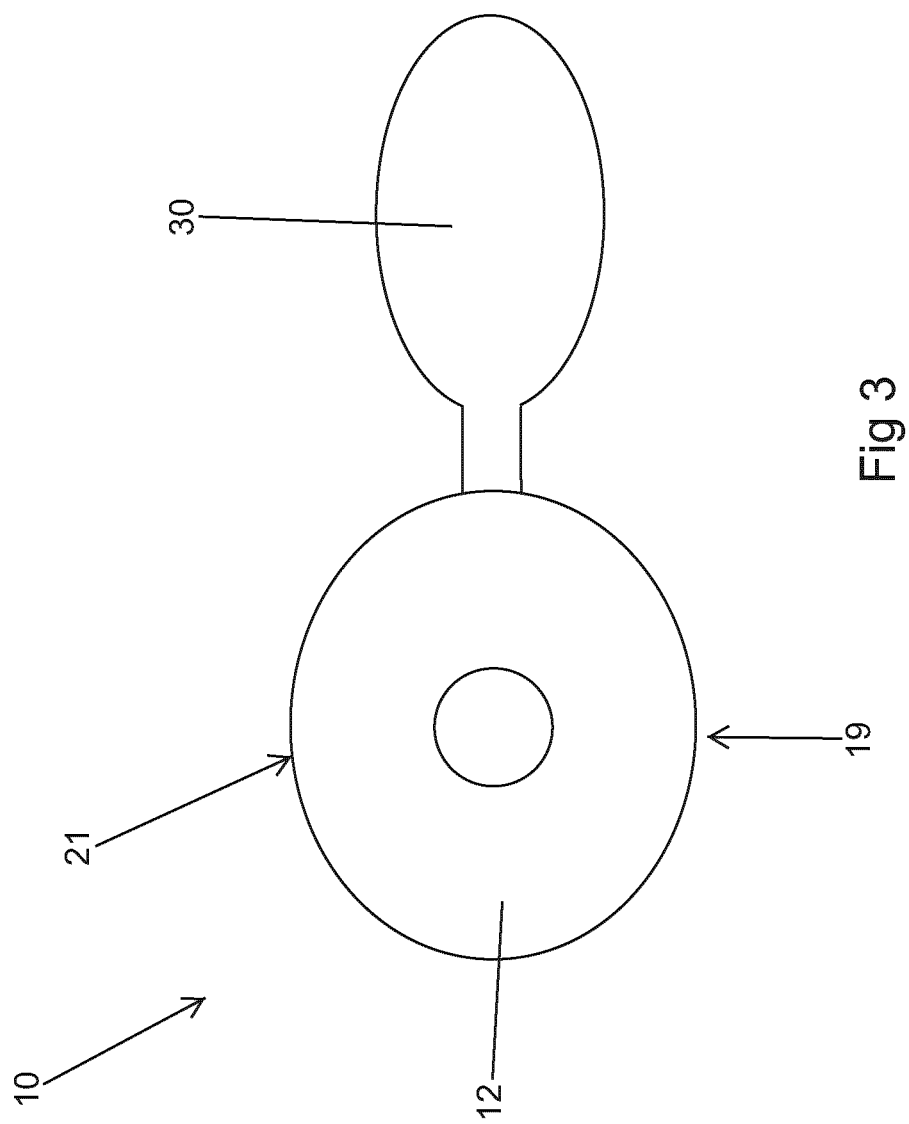
FIG. 3 is a top plan view of the negative pressure injection device of FIG. 1.

Structure and Relationship of Parts:

Referring to FIG. 1, negative pressure injection device 10 includes a suction cup 12 having a top 14 and a peripheral sidewall 16 that define an interior 18 and an exterior 20. Referring to FIG. 3, and as will hereinafter be explained, one half of a circumference of suction cup 12, generally indicated by reference numeral 19 is made from a transparent material and the other one half of the circumference of suction cup 12, generally indicated by reference numeral 21, is made from an opaque material. An injection port 22 through which liquid is injected extends from exterior 20 to interior 18 of suction cup 12. An inner skirt 24 encircles injection port 22 and depends into interior 18 of suction cup 12. An injection member 26 is in fluid communication with injection port 22. Injection member 26 is surrounded by and protrudes below inner skirt 24. A pressurization port 28 extends from interior 18 to exterior 20 of suction cup 12.

There will now be described some desirable, but non-essential preferred features. It is preferred that exterior 20 of suction cup 12 along peripheral sidewall 16 have a pressurization bulb 30 in communication with pressurization port 28. This is a simple and effective way of pressurizing interior 18. It is, however, not the only way of pressuring interior 18. For example, if suction cup 12 is flexible, this could be done by placing suction cup 12 against epidermis 200 and, squeezing and then releasing suction cup 12 to create a negative pressure within interior 18 of suction cup 12. The positioning along peripheral sidewall 16 has proven to be a convenient location for pressurization bulb 30, earlier prototypes had the pressurization bulb on top. It is preferred that exterior 20 of suction cup 12 at top 14 have an internally threaded syringe coupling 32 for coupling with external threads a standard needle-free syringe 100. Syringe coupling 32 is in fluid communication with injection port 22. It is preferred that injection member 26 is a needle. It will be understood that injection member 26 can take other "needle-less" forms as long as the liquid being injected is able to enter the skin.

Figures 6, 7:
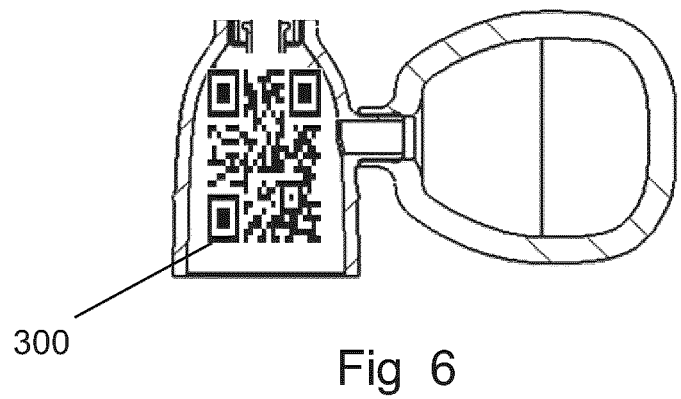
FIG. 6 is a perspective view of the negative pressure injection device of FIG. 1, with a QR code.
FIG. 7 is a flow diagram setting forth the process flow for using the negative pressure injection device with the QR code of FIG. 6.

Referring to FIG. 6, a QR code 300 can be mounted on negative pressure injection device 10.

Figure 2:
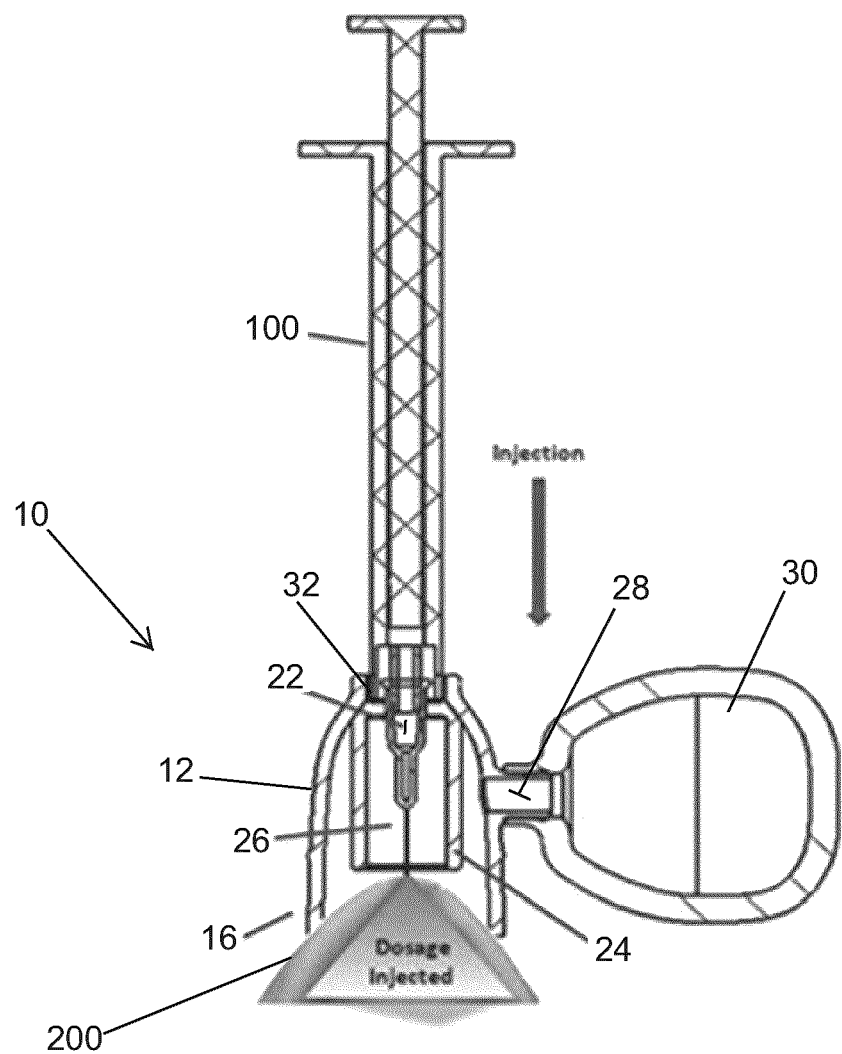
FIG. 2 is a side elevation view, in section, of the negative pressure injection device coupled with a standard needle-free syringe.

Operation:

Referring to FIG. 2, in operation, a standard needle-free syringe 100 charged with liquid is connected to syringe coupling 32 position on top 14 of suction cup 12. Suction cup 12 is then positioned on epidermis 200. Pressurization bulb 30 is then used to draw air from interior 18 of suction cup 12 through pressurization port 28. As interior 18 of suction cup is pressurized, epidermis 200 is drawn into interior 18 of suction cup 12 until epidermis 200 comes into contact with inner skirt 24 and that portion of injection member 26 protruding below inner skirt 24. Inner skirt 24 limits incursion of epidermis 200 into interior 18 of suction cup 12, thereby providing consistent epidermis positioning. The depth of injection is consistently defined by the extent to which injection member 26 protrudes below inner skirt 24. Referring to FIG. 3, it is preferred that half of circumference of suction cup 12, generally indicated by reference numeral 21, be made from an opaque material, such that injection member 26 is hidden from the sight of the patient. However, It is preferred that half of a circumference of suction cup 12, generally indicated by reference numeral 19 be made from a transparent material, such that positioning of epidermis 200 relative to inner skirt 24 may be viewed by a person administering the injection through suction cup 12. Referring to FIG. 2, once epidermis 200 is in the desired position, the standard needle-free syringe 100 is used to inject fluid. As syringe coupling 32 is in fluid communication with injection port 22, the liquid contents of needle-free syringe 100 pass through injection port 22 to injection member 26 and into epidermis 200.

It is believed that negative pressure injection device 10 is well suited for self-injection or injection by family members. The advantages that negative pressure injection device 10 provides in this regard are set forth below. In order to facilitate medical personnel monitoring an injection program that involves self-injection or injection by family members, it is preferred that negative pressure injection device 10 be provided with a QR code 300, as illustrated in FIG. 6. The injection program can then be remotely monitored, by use of an application on a smart phone or similar mobile device. The process flow for such an Application is set forth in FIG. 7. The QR code 300 is scanned at the time the injection is administered. A record of the time and date of the injection is then created by the Application. This record is accessible to medical staff who are remotely monitoring the injection program. As days, weeks and months pass, a history of the injection regimen is created and maintained.

ADVANTAGES

1. The probability of hitting an underlying organ, nerve or bone is reduced, due to consistent predetermined fixed depth of needle penetration.

2. Less training is required for medical staff, as one universally-familiar procedure for successful delivery of the injection 3. Reduced skin trauma.

4. Two-stage 'physical' sensation and distraction for the injection recipient; due to the skirt plus cup design and resulting upward pressure.

5. Needle tip remains mostly covered and away from the line-of-sight of the injection recipient.

6. Skin can be visually monitored during the entire injection process—user is able to view the epidermis 200 through the transparent suction cup 12.

7. Preliminary testing indicates less back flow (reflux) of the medication from the injection site.

8. Reduced likelihood of staff experiencing needle stick injuries.

9. May attach to any standard needle-free syringe.

10. The design configuration of negative pressure injection device 10 allows use with a thinner needle, as the design configuration of the device prevents any bending of the needle. For example, a 33 g needle.

11. The design configuration of negative pressure injection device 10 improves the safety of injections, despite movements of the patient or shaking hands of persons administering the injection. This assists patients administering their own injections or persons with reduced dexterity or cognitive capabilities who are called upon to administer injections to others.

12. A larger and softer pressure bulb can be used for increased ease of handling for cognitively challenged or age impaired patients.

Figure 4:
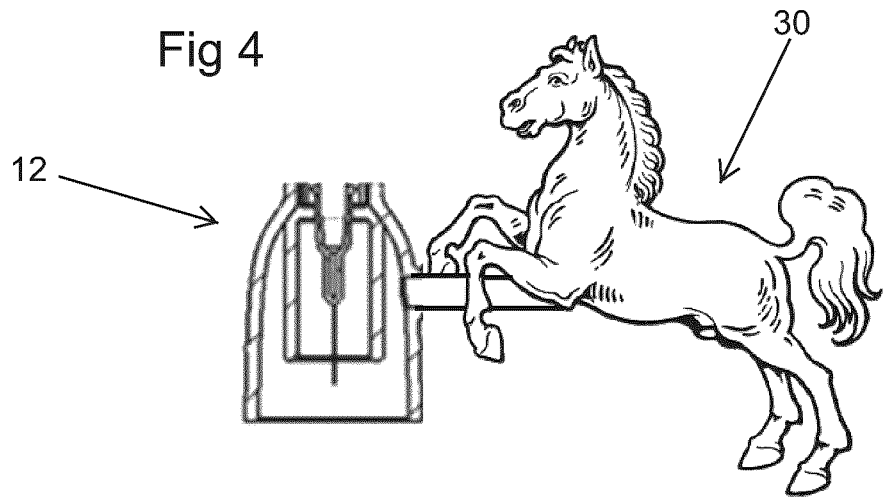
FIG. 4 is a side elevation view of the negative pressure injection device with a pressure bulb shaped like an animal.
Figure 5:
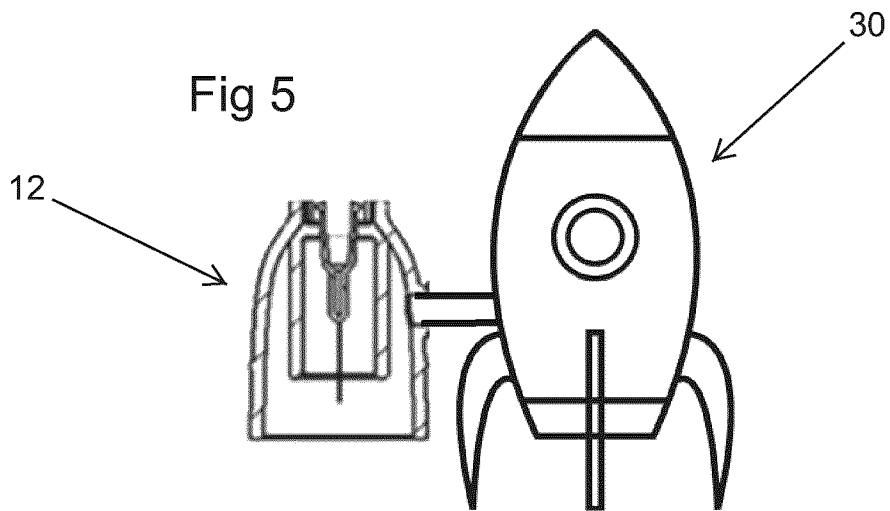
FIG. 5 is a side elevation view of the negative pressure injection device with a pressure bulb shaped like a rocket ship.

13. When intended for use in giving injections to children, the pressure bulb can be made in different shapes to distract the child. For example, the pressurization bulb can be shaped as a three dimensional representation of a creature or man-made object. Referring to FIG. 3, an animal been illustrated as a representative creature. Referring to FIG. 4, a rocket ship has been illustrated as a representative man-made object.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

The scope of the claims should not be limited by the illustrated embodiments set forth as examples, but should be given the broadest interpretation consistent with a purposive construction of the claims in view of the description as a whole.

What is claimed is:

1. A negative pressure injection device comprising:
   a suction cup having a top, a bottom and a peripheral sidewall that define an interior and an exterior;
   an injection port, through which liquid is injected, extending from the exterior to the interior of the suction cup;
   an inner skirt encircles the injection port and depends into the interior of the suction cup, and the inner skirt being spaced inwardly from the bottom of the suction cup;
   an injection member in fluid communication with the injection port, and the injection member being surrounded by and protruding below the inner skirt a fixed distance and spaced inwardly from the bottom of the suction cup; and
   a pressurization port extending from the interior to the exterior of the suction cup, such that when air is drawn from the suction cup through the pressurization port the interior of the suction cup is pressurized to draw an epidermis of a patient into the suction cup until the epidermis comes into contact with the inner skirt and that portion of the injection member protruding below the inner skirts;
   wherein approximately one half of a circumference of the suction cup is made from a transparent material such that positioning of the epidermis, relative to the inner skirt, may be viewed by a person administering an injection through the suction cup and another one half of the circumference of the suction cup is made from an opaque material such that the injection member is hidden from the sight of the patient.

2. The negative pressure injection device of claim 1, wherein the exterior of the suction cup along the peripheral sidewall has a pressurization bulb in communication with the pressurization port.

3. The negative pressure injection device of claim 2, wherein the pressurization bulb is shaped as a three dimensional representation of a creature or a man-made object.

4. The negative pressure injection device of claim 1, wherein the exterior of the suction cup at the top has a syringe coupling for coupling with a needle-free syringe, and the syringe coupling is in fluid communication with the injection port such that liquid contents of the needle-free syringe pass through the injection port to the injection member.

5. The negative pressure injection device of claim 1, wherein the injection member is a needle.

6. The negative pressure injection device of claim 1, wherein the negative pressure injection device having a computer readable code and a remote monitoring software application is provided which receives injection confirmation by scanning the computer readable code with a mobile device concurrently with the injection being administered.

* * * * *